(12) United States Patent
Dacremont

(10) Patent No.: US 8,202,089 B2
(45) Date of Patent: Jun. 19, 2012

(54) SUPRAOSSEOUS DENTAL IMPLANT

(76) Inventor: Philippe Dacremont, Toulon (FR)

( * ) Notice: Subject to any disclaimer, the term of this patent is extended or adjusted under 35 U.S.C. 154(b) by 439 days.

(21) Appl. No.: 12/515,836

(22) PCT Filed: Nov. 22, 2006

(86) PCT No.: PCT/IB2006/004088
§ 371 (c)(1),
(2), (4) Date: May 21, 2009

(87) PCT Pub. No.: WO2008/062256
PCT Pub. Date: May 29, 2008

(65) Prior Publication Data
US 2009/0317765 A1 Dec. 24, 2009

(51) Int. Cl.
*A61C 8/00* (2006.01)

(52) U.S. Cl. ......................................... 433/173

(58) Field of Classification Search .......... 433/172–176, 433/71–72, 201.1; 606/281–299, 70, 71; 623/17.17
See application file for complete search history.

(56) References Cited

U.S. PATENT DOCUMENTS

| | | | |
|---|---|---|---|
| 3,672,058 A | 6/1972 | Nikoghossian | |
| 3,925,892 A * | 12/1975 | Juillet | 433/176 |
| 4,702,697 A | 10/1987 | Linkow | |
| 4,815,974 A | 3/1989 | Scortecci | |
| 5,052,930 A * | 10/1991 | Lodde et al. | 433/173 |
| 5,312,256 A | 5/1994 | Scortecci | |
| 5,906,489 A * | 5/1999 | Khazzam et al. | 433/176 |
| 5,944,526 A | 8/1999 | Liu | |
| 2003/0003419 A1 * | 1/2003 | Ihde | 433/176 |
| 2006/0235400 A1 * | 10/2006 | Schneider | 606/69 |

FOREIGN PATENT DOCUMENTS

DE  36 13 951 A  11/1987

* cited by examiner

*Primary Examiner* — Todd Manahan
*Assistant Examiner* — Yogesh Patel
(74) *Attorney, Agent, or Firm* — Lucas & Mercanti, LLP

(57) ABSTRACT

The supra-osseous dental implant has a laminar elongated plate with a central, substantially rigid part extending perpendicular to the longitudinal axis of the elongated plate. An upright extending shank is fixed to the central part. A dental prosthetic can be fixed to the shank. The plate also has two lateral anchoring parts extending by two thin arms from each side of the central part. The arms are malleable and flexible relative to the central part such that the plate can bridge over a jawbone in a transverse direction to the bone crest. The anchoring parts are a vestibular anchoring part and a lingual or palate anchoring part. The anchoring parts have holes and recesses for positioning at least two anchoring screws in the lingual or palate side of the jaw bone and at least four anchoring screws in the vestibular side.

23 Claims, 2 Drawing Sheets

SUPRAOSSEOUS DENTAL IMPLANT

This application is a 371 of PCT/IB2006/004088 filed Nov. 22, 2006, the priority of which is hereby claimed and incorporated by reference herein.

The present invention lies in the field of dentistry and relates to a dental implant for positioning and fixing a dental prosthetic assembly onto the mandible or the maxilla, a preferred application of the implant relating to human dental implantation.

It is already common practise, in the art of dental implantation, to use endo-osseous dental implants for fixing dental prostheses. These implants can traditionally be classified in one of the following two types of implants:
  vertically insertable implants;
  laterally insertable implants.

Vertically insertable implants generally have a cylindrical or cylindro-conical shape adapted for vertical axial insertion directly into a hole mechanically drilled into a jaw bone. An upper part of the implants emerging from the bone crest holds fixing means for connecting a prosthetic assembly, said assembly comprising suitable interface means for rigidly fixing one or several dental prostheses. U.S. Pat. No. 5,312,256 discloses an example of a vertically insertable implant.

Laterally insertable implants comprise a substantially plane base, which can for example have the form of a disc or a square plate, from which extends a rod or shaft perpendicularly fixed to said base. Such implants are inserted laterally into a pair of perpendicular slots pierced in a jaw bone (mandible or maxilla) by lateral osteotomy, said base being inserted into a first substantially horizontal slot and said rod of shaft extending and sliding into a second substantially vertical slot, one end of said rod emerging from said second slot above the jaw bone crest and holding fixing means for connecting a prosthetic assembly. U.S. Pat. No. 4,815,974 discloses an example of a laterally insertable implant.

Both types of implants are today widely used by dental surgeons, with a preference in use for vertically inserted implants, which are easier to manipulate and insert. Nevertheless, these implants and their use are not completely satisfying.

A first drawback of the above-presented implants is that they cannot fit every patient who needs to be implanted. Indeed, some people suffer severe osseous resorption after loosing their original teeth. In such cases, the hardness and/or thickness of the jawbone where implantation should be carried out are not compatible with endo-osseous implantation.

Furthermore, even when thickness and hardness of the jawbone allow endo-osseous implantation, the drilling or cutting of the bone that must take place in order to position those implants create a trauma at the level of the bone. This trauma is associated with further bone loss for the patient. This can sometimes be irreversible and may lead to the rejection of the implant.

Finally, endo-osseous implantations, as they are practised today represent a certain cost that can sometimes not be supported by patients who then choose not to be implanted while they should be, leading to further damaging of their dental health.

The present invention aims at providing a new and alternative solution to implant patients to position a dental prosthetic assembly in their jawbones.

This new implant can fit any patient, regardless of the hardness and/or thickness of the jawbone where implantation should be carried out.

Another object of the invention relates to providing a dental implant that can be fixed in a jawbone and support a prosthetic assembly without cutting the bone, therefore without bone trauma.

The invention also aims at providing a dental implant that is easier to use by practitioners and surgeons, and less traumatizing for patients. Therefore, the new method of implantation related to that implant is less risky.

A further object of the invention relates to the provision of a dental implant and correlative method of implantation with a significant reduction of the involved costs.

In accordance with one aspect of the present invention, a supra-osseous dental implant is provided, comprising a laminar elongated plate comprising a central substantially rigid part bearing an upright extending shank fixed to said central part. The shank comprises means for fixing a dental prosthetic assembly, and said plate also comprises two lateral anchoring parts edging said central part and being malleable and flexible relative to said central part, such that said plate can be bridged over a jawbone. The anchoring parts comprise a vestibular anchoring part and a lingual or palate anchoring part, and also comprise means for positioning at least two anchoring screws in the vestibular side and lingual or palate side of said jaw bone.

Specifically designed for supra-osseous implantation on maxilla or mandible jawbones the implant of the invention proves very advantageous as it eliminates the need to first cut or drill in the bone to set the implant in. Thus, implantation using the implant of the invention is less traumatizing for patients. The implant is only fixed by osseointegrable screws fixing the anchoring parts against the vestibular and lingual or palate sides of the jawbone.

The implant of the invention is characterized by its two lateral anchoring parts, which are flexible and malleable relative to the central part of the implant bearing the shank. Thanks to these two malleable parts the implant can thus be bridged in a transverse direction over the bone crest like a saddle, and be fixed onto the vestibular and lingual or palate sides of the jawbone by osseointegrable screws, without insertion of the implant itself in the jaw. The flexibility of the elongated plate allows a perfect fit of the implant over the cortical bone crest in both sagittal and front directions.

The vertical part of the implant, the shank, comprises a trans-gum base connector fixed to the central part of the plate at the factory stage and a dismountable prosthetic or print pillar that is adapted to be plugged onto said base connector and fixed by a screw. Advantageously, said pillar comprises means for fixing a dental prosthetic assembly.

According to a preferred configuration of the implant of the invention, the above-mentioned base connector is made of two parts: a lower part having a smooth surface and a cylindro-conical upper part adapted to engage, preferably in abutment, with a complementary female portion of said pillar. Such a cylindro-conical connector facilitates alignment of the pillar and the base connector. Furthermore, the smooth surface of the base connector and the pillar prevents the pillar from grating the gum after implantation.

According to another advantageous characteristic of the invention, the upper part of the base collector and the corresponding female part of the pillar both comprise a central bore. Those two central bores correspond with each other when the base connector is engaged with the pillar. Once they fit, the bores receive a locking screw to secure the pillar to the base connector. This system ensures an easy maintenance and dismantling of the pillar when needed.

In a preferable embodiment of the implant said pillar comprises a trans-gum lower part having a smooth external surface and an upper prosthetic part having a rough external surface. Such rough external surface may be obtained by means of sand treatment of the pillar's surface. It enhances the fixing of prostheses with resins or glues on the pillar.

Preferably, the pillar of the shank of the implant of the invention is cuttable, in order to allow depth adjustment of the prosthesis in relation with the other teeth of the implanted patient once the implant has been fixed on the jawbone.

Preferably again, said external surface of said upper prosthetic part of said pillar comprises threads and/or crests.

Another specific configuration of the implant of the invention lies in its elongated plate wherein the vestibular anchoring part is longer than the lingual or palate anchoring part. Both anchoring parts comprise at least two peripheral holes adapted for receiving an anchoring screw in order to fix said anchoring part to the vestibular and lingual or palate sides of a jawbone.

Thanks to these holes, the implant of the invention can be fixed on a jawbone via some screws without cutting-out bone to insert the implant directly inside. The fixing of the implant of the invention is therefore far less harmful for patients than the implants of the prior art.

In order to increase the number of available positions for threading anchoring screws in the jaw, the anchoring parts also comprise at least one curved recessed portion, or notch, said portion being tapered for adjustment in abutment of an anchoring screw collar. As a reference, the vestibular anchoring part comprises at least twelve means (holes and/or notches) for positioning anchoring screws and the lingual or palate anchoring part comprises at least six means (holes and/or notches for positioning anchoring screws. On the vestibular anchoring side, the preferred configuration is at least four peripheral holes, preferably placed in a square configuration and eight recessed portions of notches. Nevertheless, other configurations can involve different combinations of holes and notches, the holes being placed according to different configurations depending on their number (triangle, hexagon, pentagon, rectangle, circle, aligned, in T shape, in U shape, in X shape . . . etc.).

On both anchoring parts, vestibular and lingual or palate, the number of means used to position anchoring screws can vary whatever combination is made of notches and holes, provided both sides present at least two holes. This is the only way to eliminate any implant mobility through rotation.

According the invention, said vestibular anchoring part also comprises a central notch positioned close to the pillar and the central rigid part for receiving an adjustment screw. Contrary to the other notches or recessed portions on the elongated plate, where screws can only be set in one position, this notch is configured to offer different setting possibilities, in collaboration with a said adjustment screw, of the position of said central part of the implant above the crest of said jaw bone before fixing said anchoring parts.

The goal of said central notch is to be able to position the adjustment screw without any interference with an anchoring screw set on the opposite palate or lingual side of the jawbone.

Other preferable characteristics of the invention include the following:
  said vestibular anchoring part comprises a four-leaves-shamrock-shaped cut-out between said four peripheral holes, the circular peripheral flanges of said cut-out being tapered to allow adjustment of up to four anchoring screws into said cut-out.
  said elongated plate and said shank are made titanium.
  said elongated plate and said shank have been treated by anode oxidization.
  the thickness of said elongated plate is about 0,2 millimeters to 1 millimeters, preferably about 0,4 mm to 0,8 mm.
  the length of said elongated plate is about 20 to 35 mm, and preferably about 24 mm to 34 mm.

The present invention also relates to a kit for dental implantation comprising a supra-osseous dental implant according to the invention as previously depicted above and at least four osseointegrable screws for adjusting and anchoring said dental implant onto a maxilla or mandible jawbone. Preferably, said kit for dental implantation comprises up to eighteen osseointegrable screws for adjusting and anchoring said dental implant onto a maxilla or mandible jawbone.

The implant of the invention will now be described in relation with the following drawings amongst which:

Figure 1:
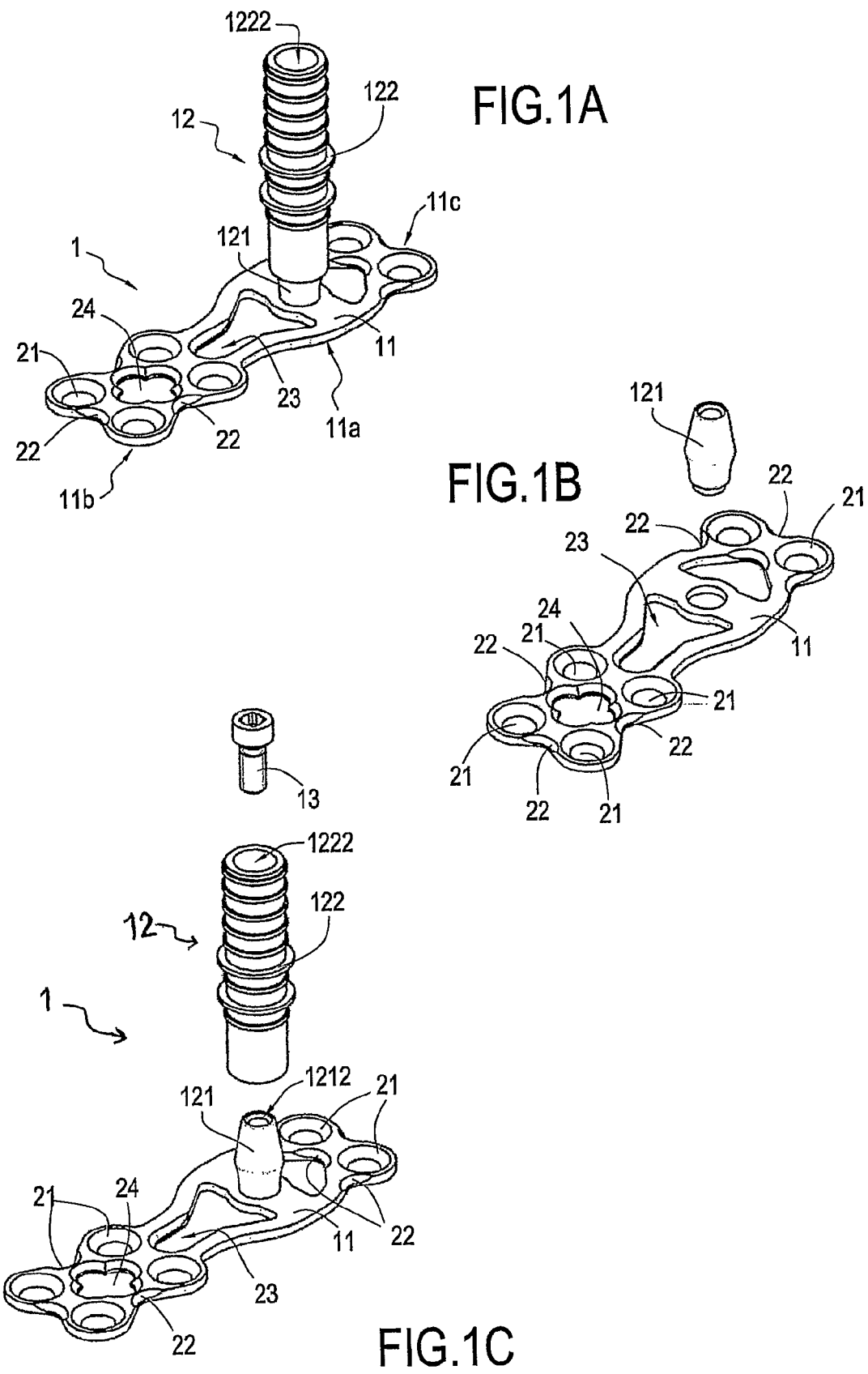
FIGS. 1A and 1B, 1C are respectively an assembled view and exploded views of the implant of the invention.

FIGS. 1A, 1B and 1C show a supra-osseous dental implant 1 according to the present invention, comprising a laminar elongated plate 11 bearing an upright extending shank 12.

For the implant to be implantable on a vast majority of patients (children, adults, elderly people), the thickness of said elongated plate 11 of the implant 1 lies between 0,2 millimeters to 1 millimeters, its length is about 20 to 35 mm and its width is about 5 to 10 mm. Preferable embodiments of the implant show a plate 11 having a thickness of about 0,4 mm to 0,8 mm, a length of about 24 mm to 34 mm, for a width of about 7,5 to 10 mm.

Figure 2:
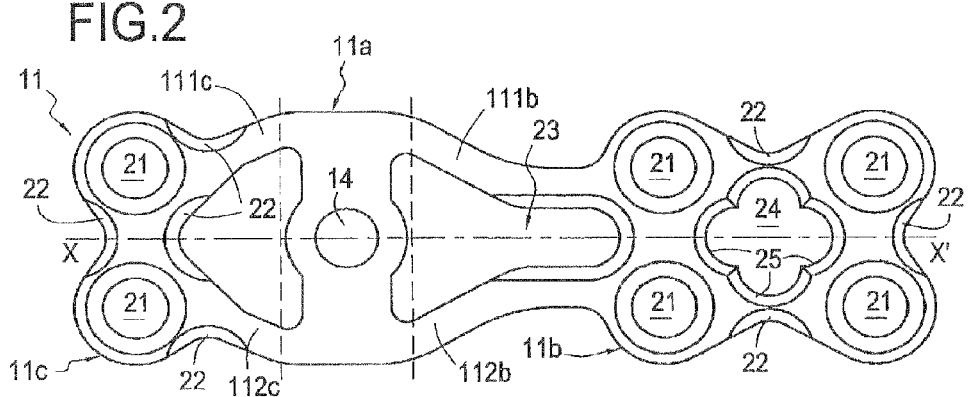
FIG. 2 is a plan view of the fixing plate of the implant of the invention, without its trans-gum base connector and print or prosthetic pillar.
Figure 3A:
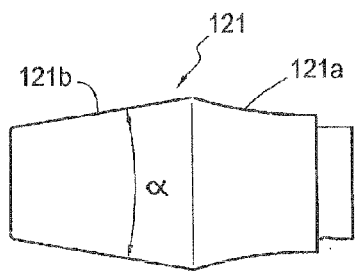
FIGS. 3A and 3B are respectively a plan and a cross-sectional view of the trans-gum base connector assembled at the factory stage onto the fixing plate for fixing a print or prosthetic pillar.
Figure 3B:
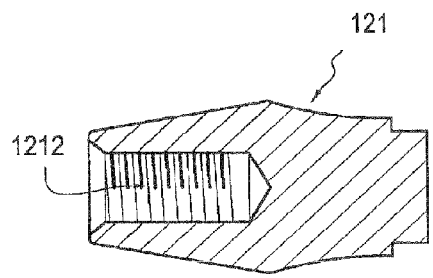

According to FIG. 2, the elongated plate 11 comprises a central substantially rigid part 11a having a substantially rectangular shape and extending perpendicularly to the longitudinal axis XX' of said plate 11. The central part 11a comprises a central bore 14 adapted to receive in abutment a base connector 121 as shown in FIGS. 3A, 3B, said base connector being welded at the manufacturing stage onto the plate 11.

On each side of the central part 11a, along said longitudinal axis XX', extends an anchoring part 11b, 11c designed to fix the implant 1 onto a maxillary or mandible jawbone. Those anchoring parts 11b, 11c extend respectively from said central part 11a by two thin arms 111b, 112b; 111c, 112c on each side. Those arms give the anchoring parts enough malleability and flexibility relative to the central part so that the plate can be bent about the edges of the central part 11a delimited in dashed lines on FIG. 2. The implant 1 can be bridged over a jawbone, thanks to anchoring parts 11b, 11c, those parts comprising a vestibular anchoring part 11b that is longer than the lingual or palate anchoring part 11c.

Figure 5:
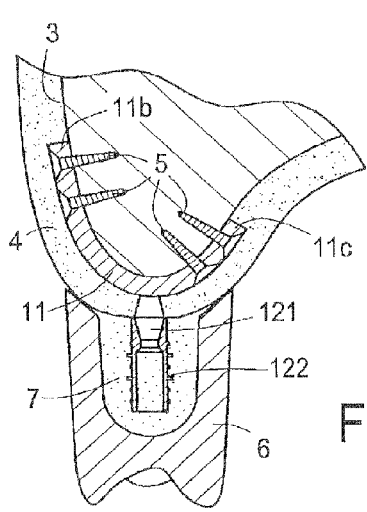
FIG. 5 is a cross-sectional view of a maxillary jaw implanted with the implant of the invention and a tooth prosthesis fitted onto said implant.

The anchoring parts 11b, 11c comprise several means 21, 22, 23, 24, 25 to position the osseointegrable anchoring screws in the vestibular side and lingual or palate side of the jawbone. Those screws fix the implant 1 over the jawbone crest 3 as shown in FIG. 5 for a maxillary implantation.

Those means used to position the anchoring screws advantageously comprise peripheral holes 21 and curved recessed portions or notches 22, said holes 21 and said recessed portions 22 being tapered to facilitate adjustment in abutment of an osseointegrable screw collar.

In the preferred embodiment shown in the figures, the vestibular anchoring part 11b comprises at least four peripheral holes 21 placed in a substantially square configuration with one recessed portion 22 formed between each hole 21 on the outside edge of the plate. It also comprises an inner four-leaves-shamrock-shaped cut-out 24 centred with said four peripheral holes 21. The circular peripheral flanges 25 of said cut-out 24 are tapered like the outer portions 22 to allow adjustment of up to four anchoring screws into said cut-out. It finally comprises a central notch 23 that will receive an adjustment screw.

In the same preferred embodiment, said lingual or palate anchoring part 11c comprises two peripheral holes 21 and four recessed portions 22.

Thus, the implant shown in the figures comprises twelve means 21, 22, 23, 24, 25 for positioning osseointegrable anchoring screws in the vestibular anchoring part 11b and six means 21, 22 for positioning anchoring screws in said lingual or palate anchoring part. This gives surgeons lots of possibilities to fix the implant in a supraosseous manner on a jawbone crest where the quality and thickness of the bone is the best, without cutting in the bone what is traditionally very traumatizing for the patient.

The elongated plate 11 and the shank 12 are preferably made of a titanium alloy, which is a biocompatible metallic alloy with a high mechanical strength. Preferably, the elongated plate 11 and the shank 12 have been treated by anode oxidization to modify the light reflection properties on their surfaces.

Thanks to this oxidization treatment the elongated plate 11 and base connector 121 show a red colour in order to prevent colour interferences when the gum is particularly thin at the implantation level. In the same vain, said pillar 122 is made of titanium that has been treated so as to present a yellow colour that will not interfere with the colour of the surrounding teeth.

The shank 12 of the implant 1 is aimed at receiving a dental prosthetic assembly 6 as shown on FIG. 5. As shown in FIGS. 1B and 1C, said shank 12 is made of a trans-gum base connector 121, which is fixed onto the plate 11 of the implant, and a dismountable print of prosthetic pillar 122. The prosthetic or print pillar 122 is adapted to be plugged onto the trans-gum base connector 121 and secured thereto by means of a locking screw 13.

Said base connector 121 is preferably mounted in abutment into the central bore 14 of said central part 11a of said elongated plate 11 of the implant 1 and secured onto said plate by a laser weld at the factory.

Figure 4:
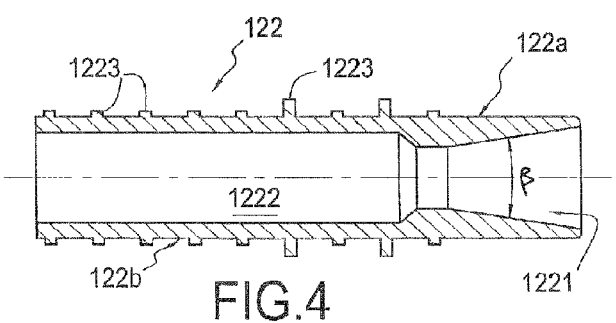
FIG. 4 is a cross-sectional view of a print or prosthetic pillar to be fixed onto the trans-gum base connector of the implant of the invention.

As shown in FIGS. 3A, 3B and 4, the base connector 121 comprises a lower part 121a presenting a smooth surface and a cylindro-conical upper part 121b adapted to engage in abutment with a complementary female portion 1221 of said pillar 122.

The upper part 121b of said base collector and the complementary female portions 1221 of said pillar 122 both comprise a central bore 1212, 1222 to receive said locking screw 13, said bore 1212 being threaded.

The angle α between the flanges of said cylindro-conical upper part 121b of the base connector is substantially equal to the angle β of the female portion 1221 of said pillar 122 to allow a perfect alignment of said pillar onto said base connector such that bores 1212, 1222 correspond with each other to receive said locking screw 13 and secure the pillar to the base connector 121.

Moreover, said pillar 122 comprises a trans-gum lower part 122a presenting a smooth external surface and an upper prosthetic part 122b presenting a rough external surface. Said upper prosthetic part 122b comprises threads and/or crests 1223 for fixing a dental prosthetic assembly. The trans-gum lower part 122a has a smooth surface to provide a better integration of the implant at gum level. This is also a way to limit the risk of bacterial retention at this level.

On the contrary, the upper prosthetic part 122b of the pillar has a rough surface obtained, for example, by sand blasting of the surface. This rough surface associated with said threads and/or crests 1223, improves the grasping of the resin or glue 7 used to fix a dental prosthetic assembly 6 on shank 12 of the implant 1 as shown in FIG. 5.

Preferably, the pillar 122 is also chosen cuttable, for example with a diamond saw or a drill, so that the total length of the shank 12, which is about 15 mm, can be adjusted to fit any prosthesis or to take a print of an appropriate prosthesis.

The structure and the shape of the plate 11 of the implant 1, which among other things sit the implant on the hard cortical part of the jawbone, confer a great mechanical strength on the ensemble. This makes implanting great prosthetic assemblies easier, with only a few implants. For example, a complete maxillary or mandible prosthesis with 16 teeth can be fixed onto the maxillary or mandible jaw of a patient equipped with only four supraosseous implants 1 of the invention. It is recalled here that, when using traditional endo-osseous implants, that sit mainly on the spongy part of the bone, it is necessary to put more implants (generally between 8 and 12 implants) in order to support identical prosthetic assemblies.

Moreover, the use of the implant of the invention doesn't require heavy osseous surgery to be carried out before implantation. Thus, surgeons can avoid maxillo-mandibular anatomical obstacles and treat patients with high osseous resorption. At the level of the upper maxillary this also eliminates the need to carry out sinus lifts (bone grafting). At the posterior mandible level this eliminates the need to translate the mandibular nerve. Thus the use of the implant 1 of the invention eliminates a lot of heavy surgical risks.

The implant 1 of the invention is also very easy to place and fix onto a jawbone with appropriate osseointegrable screws. The multiple holes 21 and recessed portions 22, 25 in the anchoring parts 11b, 11c of the plate 11 of the implant, added to the flexibility of said plate 11, give the surgeon carrying out the implantation a great choice of positions for the anchoring screws in both front and sagittal planes.

A method of implantation will now be described with reference to FIG. 5 showing a cross-section of a maxillary jaw bone 3 implanted with the implant of the invention and a tooth prosthesis 6 fitted onto said implant.

First, the surgeon opens and detaches the gum 4, creating a mucoperioste strip, where the implant 1 is to be set. This provides an opening in the gum 4 through which the surgeon can have access to the jawbone 3. Second, the surgeon introduces the implant 1 into the opening in the gum 4 using appropriate pliers. With said pliers, the surgeon then positions the implant 1 over the jawbone crest in such a way that the central rigid part 11a rests on the top of the bone crest with the trans-gum base connector 121 extending through the opening in the gum perpendicular to the bone crest.

The anchoring parts 11a, 11b of the plate 11 of the implant are then, in a third time, forced with said pliers against the vestibular side and palate side of the jawbone 3. The implant is then secured with osseointegrable screws 5 that are threaded into the bone 3. The position of said screws 5 is determined by using a combination of the holes 21, recessed portions 22 and flanges 25 present in said anchoring parts 11b, 11c of the plate 11 of the implant. One way to ease the fixing of the anchoring parts 11b, 11c is to first position the implant over the bone crest with an osseointegrable screw threaded into said notch 23 in the vestibular anchoring part. This stabilizes the implant over the jawbone before inserting the other anchoring screws 5 into the anchoring parts 11b & 11c. It is mandatory to use at least two screws on the vestibular anchoring part, and two others on the palatine or lingual anchoring part, this in order to eliminate any risk of implant rotation. This also ensures a better anchoring of said implant.

For the sake of clarity, only two screws (the minimum required amount of screws) 5 have been represented in FIG. 5 for fixing each anchoring part 11b, 11c. However, the total number of screws 5 to be used must be determined clinically by the surgeon. It depends on the density of the bone and the thickness of the jawbone crest at the point of implantation. Furthermore, the use of screws of variable length can also improve the fixation of the implant, depending on the quality and quantity of the jawbone 3. The use of a greater number of screws 5 improves the tightness of the implant onto the bone 3, and prevents the rotation of the implant.

After that, the surgeon only has to close and suture the opening in the gum around the trans-gum base connector 121 protruding through the gum.

Once the gum 4 has been sutured, the next stage is dedicated to the prosthesis itself. First the pillar 122 of the shank 12 is mounted onto said base connector 121 with an appropriate locking screw 13 (not shown in FIG. 5). Then, there are several available techniques. One consists of directly fixing a tooth prosthesis 6 that has been previously prepared onto the pillar 122. Another one consists of making a print of the gum 4 and pillar(s) 122 in order to prepare a tooth prosthesis or a bridge custom fitted.

The fixing of the tooth prosthesis 6 or bridge onto said pillar 122 is made with resin or glue 7 bonded into the pillar and the prosthesis cavity, said resin and glue 7 adhering to the rough surface of the pillar and of the prosthesis.

Using the new supraosseous implant 1 of the invention, an experimented surgeon can complete the implantation and prosthetic operations in only one to two hours. The patient is able to eat normally only a few hours later.

The use of the implant 1 of the invention permits a real gain of time for the implantation process and is easier. It also presents a much lesser risk for the patient. This ultimately reduces drastically hospital and prosthetic costs for the patients. As a result, more patients will have access to permanent prostheses that are more comfortable and less harmful, particularly for the gum tissues, than mobile prostheses.

Due to the configuration of the implant, with several possible positions for the screws 5, the surgeon can chose the screws locations so as to use the densest osseous parts of the jawbone 3.

Besides, the implant of the invention, thanks to its numerous screw threading possibilities, can be set in any type of bone: basal or alveolar. Therefore, even if all the alveolar bone has disappeared due to bone resorption, the implant can still be in a satisfying way. Therefore, the implant can be set in jaws with a reduced bone height, and even when no crest bone is available.

In most of the cases, surgeons will have to use only a few screw-positioning means 21, 22 on each anchoring part 11b, 11c of the implant 1. The positioning means that are not used for the original anchoring of the implant remain available for future use in case, for example, of failure of the osseointegration of one of the anchoring screws. This allows keeping the implant and just threading another screw in, whereas, with cylindrical endo-osseous implants, the implant would have to be replaced, as well as the prosthesis.

Another advantage of the implant of the invention lies in its possible use as temporary implant. This may be useful for surgeons who prefer to use a more classical implantation method, said method comporting two phases: the implantation per se in a first time, followed by the prosthetic phase around six months later.

Moreover, in case of a failing implant in a multiple-implant configuration (e.g. broken implant), this new system allows to save the prosthetic work. In this case it is just necessary to unscrew the broken prosthetic ensemble from all the implants and to take it out of the mouth. The broken implant is removed from the mouth. Still outside of the mouth, a new implant is set on the prosthetic ensemble. This new set (new implant + prosthetic ensemble) is then set back into the patient's mouth. The exact position of the new implant is then found by setting the prosthetic ensemble on the remaining implants that are used as a surgical guide. Therefore, the implant of the invention is the only one to allow saving most of the work in case of problems.

Another advantageous characteristic of the implant of the invention relates to its flexibility after implantation onto a jawbone. Indeed, in spite of its important retention on the vestibular and palate or lingual side of the jawbone due to the use of osseointegrable screws 5, the central part 11a of the implant 1 remains flexible by a few tenths of millimeters over the bone crest. In fact, there is a bit of play between the rigid part of the implant and the bone crest, because the implant cannot totally adopt the shape of the crest. This play gives the ensemble a light flexibility. This eases the prosthetic integration in comparison with actual rigid implants and prostheses.

This new implant 1 is therefore unique because it is the only one to reproduce the relative natural elasticity of the human teeth. As a result, it is possible to envisage the use of mixed bridges that would be set both on implants and teeth. So far, with all the other systems, this mix of bridge supports is strongly inadvisable.

It should be noted that the embodiment of the invention has been described above in reference to the figures purely by way of example. Many other modifications and developments may be made thereto within the scope of the present invention.

The invention claimed is:

1. A supra-osseous dental implant comprising:
   (a) a laminar elongated plate having a longitudinal axis, said elongated plate having:
      (i) a vestibular anchoring part at one end of the elongated plate, the vestibular anchoring part having a first means for positioning at least four anchoring screws in a vestibular side of a jaw bone,
      (ii) a lingual or palate anchoring part at the other end of the elongate plate, the lingual or palate anchoring part having a second means for positioning at least two anchoring screws in a lingual or palate side of the jaw bone,
      (iii) a substantially rigid, central part positioned between the vestibular anchoring part and the lingual or palate anchoring part, the central part extending perpendicular to the longitudinal axis,
      (iv) a first and second thin arm extending along the longitudinal axis and connecting one side of the central part to the vestibular anchoring part,
      (v) a third and fourth thin arm extending along the longitudinal axis and connecting the other side of the central part to the lingual or palate anchoring part; and (vi) the first and second thin arm and the third and fourth thin arm being malleable and flexible relative to the central part such that the elongate plate can bridge over the jawbone, in a transverse direction to a bone crest, and b) an upright extending shank fixed to the central part, the shank having a means for fixing a dental prosthetic to the shank.

2. The supra-osseous dental implant according to claim 1, wherein said vestibular anchoring part is longer than said lingual or said palate anchoring part.

3. The supra-osseous dental implant according to claim 1, wherein the first and second means comprise at least two peripheral holes.

4. The supra-osseous dental implant according to claim 1, wherein said first and second means comprise at least one curved recessed portion, said portion being tapered for adjustment in abutment of an anchoring screw collar.

5. The supra-osseous dental implant according to claim 1, wherein said first means comprises at least four peripheral holes.

6. The supra-osseous dental implant according to claim 1, wherein said first means positions at least twelve anchoring screws and said second means positions at least six anchoring screws.

7. The supra-osseous dental implant according to claim 1, wherein said vestibular anchoring part comprises a central notch for receiving an adjustment screw, said notch being configured to set, in collaboration with a said adjustment screw, position of said central part of the implant above the bone crest of said jaw bone before fixing said vestibular and lingual or palate anchoring parts into said vestibular and said lingual or palate side of said jaw bone.

8. The supra-osseous dental implant according to claim 1, wherein said first means is four peripheral holes and a cut-out in the shape of a four-leaves-shamrock, the cut-out positioned between said four peripheral holes, the cut-out having tapered, circular, peripheral flanges to allow adjustment of up to four anchoring screws into said cut-out.

9. The supra-osseous dental implant according to claim 1, wherein said shank comprises a trans-gum base connector fixed to said central part of said plate and a dismountable pillar adapted to be plugged onto said base connector, said pillar comprising the means for fixing a dental prosthetic.

10. The supra-osseous dental implant according to claim 9, wherein said base connector comprises a lower part having a smooth surface and a cylindro-conical upper part adapted to engage with a complementary female portion of said pillar.

11. The supra-osseous dental implant according to claim 10, wherein said upper part of said base collector and said pillar both comprise a central bore corresponding with each other when said base connector is engaged with said pillar, said corresponding bores receiving a locking screw securing said pillar to said base connector.

12. A kit for dental implantation comprising the supra-osseous dental implant according to claim 11, wherein said upper part of said base collector and said pillar both comprise a central bore corresponding with each other when said base connector is engaged with said pillar, said corresponding bores receiving the locking screw securing said pillar to said base connector, wherein eighteen osseointegrable screws for adjusting and anchoring said dental implant onto a maxilla or mandible jaw bone are provided.

13. The supra-osseous dental implant according to claim 9, wherein said pillar comprises a trans-gum lower part having a smooth external surface and an upper prosthetic part having a rough external surface.

14. The supra-osseous dental implant according to claim 13, wherein said external surface of said upper prosthetic part of said pillar comprises threads and/or crests.

15. The supra-osseous dental implant according to claim 9, wherein said pillar is cuttable.

16. The supra-osseous dental implant according to claim 1, wherein said elongated plate and said shank are made of titanium.

17. The supra-osseous dental implant according to claim 16, wherein said elongated plate and said shank have been treated by anode oxidization.

18. The supra-osseous dental implant according to claim 1 wherein the thickness of said elongated plate is about 0.2 mm to 1 mm.

19. The supra-osseous dental implant according to claim 18, wherein the thickness of the elongated plate is about 0.4 mm to 0.8 mm.

20. The supra-osseous dental implant according to claim 1, wherein length of said elongated plate is about 20 mm to 35 mm.

21. The supra-osseous dental implant according to claim 20, wherein the length of the elongated plate is about 25 mm to 34 mm.

22. A kit for dental implantation comprising the supra-osseous dental implant according to claim 1, and at least four osseointegrable screws for adjusting and anchoring said dental implant onto a maxilla or mandible jaw bone.

23. The supra-osseous dental implant according claim 1, wherein said first means comprises at least four peripheral holes placed in a square configuration.

* * * * *